US005620729A

United States Patent [19]

Watanabe et al.

[11] Patent Number: 5,620,729

[45] Date of Patent: Apr. 15, 1997

[54] METHOD OF FREEZING A SUBSTANCE USING XANTHOMONAS CAMPESTRIS FERM BP-4191 TO FORM AN ICE-NUCLEUS

[75] Inventors: Michiko Watanabe, Higashimurayama; Takahiro Makino, Hamamatsu; Kazuo Honma, Tama, all of Japan

[73] Assignee: Q. P. Corporation, Tokyo, Japan

[21] Appl. No.: 429,118

[22] Filed: Apr. 26, 1995

Related U.S. Application Data

[62] Division of Ser. No. 290,771, filed as PCT/JP93/00217, Feb. 23, 1993, Pat. No. 5,532,160.

[30] Foreign Application Priority Data

Feb. 24, 1992 [JP] Japan .................................... 4-36665

[51] Int. Cl.$^6$ .............................. C12N 1/12; C12N 1/20; A21D 4/00

[52] U.S. Cl. ...................... 426/327; 435/253.6; 435/822; 435/910; 435/252.1; 426/384; 424/93.4; 162/54

[58] Field of Search .............................. 162/54; 426/327, 426/384; 435/822, 910, 252.1, 253.6; 424/93.4

[56] References Cited

U.S. PATENT DOCUMENTS 4,978,540 12/1990 Lee .......................................... 426/61

5,194,269 3/1993 Lee .......................................... 426/61

OTHER PUBLICATIONS

Honma K., et al, INSERM (National Institute of Health and Medical Research) Colloquium, vol. 224, High Pressure and Biotechnology, "High pressure sterilization of *Xanthomonas campestris* INXC-1 as the ice nucleation active bacteria and its application to egg products", abstract, p. 292, paragraph 1, p. 292, paragraph 4—paragraph 5, p. 292, last paragraph, p. 293, paragraph 2 (Balny, C., et al. (eds.)).

*Primary Examiner*—David M. Naff
*Assistant Examiner*—Deborah Ware
*Attorney, Agent, or Firm*—Oblon, Spivak, McClelland, Maier & Neustadt, P.C.

[57] ABSTRACT

The present invention provides a new ice nucleus-forming bacterium strain, *Xanthomonas campestris* INXC-1 (FERM BP-4191), a process for the cultivation of the new ice nucleus-forming bacterium, an ice nucleus-forming substance containing the ice nucleus-forming bacterium, and the uses of the ice nucleus-forming substance. In particular a method for freezing a substance is disclosed wherein the strain FERM BP-4191 is incorporated into an ice nucleus forming substance and added to a food substance. For example, the addition is conducted by contacting the surface of the substance or by blending, or by pouring thereon the ice nucleus forming substance onto the substance to be frozen.

8 Claims, No Drawings

METHOD OF FREEZING A SUBSTANCE USING XANTHOMONAS CAMPESTRIS FERM BP-4191 TO FORM AN ICE-NUCLEUS

This is a Division of application Ser. No. 08/290,771, filed as PCT/JP93/00217, Feb. 23, 1993, now U.S. Pat. No. 5,532,160.

TECHNICAL FIELD

The present invention relates to a new strain of an ice nucleus-forming bacterium, a process for the cultivation of the new strain of the ice nucleus-forming bacterium, an ice nucleus-forming substance containing the strain, and the uses of the ice nucleus-forming substance.

BACKGROUND ART

As bacteria for promoting the formation of ice, *Pseudomonas syringae* and *Erwinia ananas* have hitherto been well known. Also, among *Xanthomonas campestris* bacteria, those known are the following three strains: the strain obtained from the leaves of Florida citrus [Goto Masao et el., Nisshokubyo-Hou, 54, 196 (1988); and Minsavage G. V. & Stall R. E., (1986), Proc. 6th Int. Conf. Plant Path. Bact., 994–1004], *X. campestris* pv. translucens [Kim H. K., Orser C., Lindow S. E. and Sands D. C., Plant Disease, 71, 994–997 (1987)], and the strain obtained from tea buds (INAX) [Goto Masao et el., Nisshokubyo-Hou, 54, 189–197 (1988)].

However, among these ice nucleus-forming bacteria, *Pseudomonas syringae* which is utilized for practical use is known to have phytopathogenicity, so that it may adversely affect the environment when it is used for spraying to form artificial snow. On the other hand, bacteria having no such phytopathogenicity generally grow slowly and thus may not be suitable for production on an industrial scale. Additionally, bacteria which are negative with respect to tobacco hypersensitivity reaction [Phytopathology, 77, 611–615 (1987)] are generally free of phytopathogenicity.

It would therefore be extremely advantageous to the industry to discover a strain which is negative with respect to tobacco hypersensitivity reaction and yet can grow at a high rate.

An object of the present invention is to provide a new ice nucleus-forming bacterium which has the above advantages. Another object of the present invention is to provide a process for the cultivation of the new ice nucleus-forming bacterium. Still another object of the present invention is to provide an ice nucleus-forming substance containing the new ice nucleus-forming bacterium and further to develop uses thereof in various fields.

DISCLOSURE OF THE INVENTION

The present inventors have conducted extensive researches for the purpose of attaining the above stated objects. As a result, they have found that a bacterium strain obtained from tea leaves is a new strain which can fulfil the intended purpose, and have thus developed the present invention.

The present invention provides a new *Xanthomonas campestris* strain, INXC-1 (FERM BP-4191).

The present invention also provides a process for the cultivation of *Xanthomonas campestris* INXC-1.

The present invention further provides an ice nucleus-forming substance containing *Xanthomonas campestris* INXC-1 and presents uses thereof in various fields.

BEST MODES FOR CARRYING OUT THE INVENTION

The bacterium strain of the present invention (referred to hereinafter as "the present strain") has bacteriological properties as shown below. In this context, strains have been classified with the use of the following culture media 1–19 (numericals are based on % by weight).

Medium 1: meat extract 1.0; bactopeptone 1.0; NaCl 0.5; bactoagar 1.5 (pH 7.2)

Medium 2: meat extract 1.0; bactopeptone 1.0; NaCl 0.5 (pH 7.2)

Medium 3: meat extract 1.0; bactopeptone 1.0; NaCl 0.5; gelatin 1.0 (pH 7.2)

Medium 4: bactolitmus milk 10.0

Medium 5: bactopeptone 1.0; $KNO_3$ 0.1

Medium 6: bactopeptone 1.0; $NaNO_3$ 0.1

Medium 7: bactopeptone 1.0; NaCl 0.5; D-glucose 0.5 (pH 7.0)

Medium 8: bactopeptone 1.0

Medium 9: TSI agar (manufactured by Eiken Chemical Co., Ltd.): indicated amount

Medium 10: meat extract 1.0; bactopeptone 1.0; NaCl 0.5; soluble starch 0.2; bactoagar 1.5 (pH 7.2)

Medium 11: $NaNH_4$ $HPO_4.4H_2O$ 0.15; $KH_2PO_4$ 0.1; $MgSO_4.7H_2O$ 0.02; citric acid 0.25 (pH 6.8)

Medium 12: Christensen medium (manufactured by Eiken Chemical Co., Ltd.): indicated amount Medium 13: D-glucose 1.0; $KH_2PO_4$ 0.1; $MgSO_4.7H_2O$ 0.05; HCl 0.02; nitrogen sources 0.1 (pH 7.2)

(Nitrogen sources are sodium nitrate and ammonium sulfate.)

Medium 14: Bacto Pseudomonas Ager F medium (manufactured by Difco): indicated amount Medium 15: urea medium (manufactured by Eiken Chemical Co., Ltd.): indicated amount Medium 16: paper filter for cytochrome oxidase test (manufactured by Nissui Seiyaku)

Medium 17: 3% aqueous hydrogen peroxide

Medium 18: OF basal medium (manufactured by Difco): indicated amount

Medium 19: $(NH_4)_2HPO_4$ 0.1; KCl 0.02; yeast extract 0.02; $MgSO_4.7H_2O$ 0.02; bactoagar 2.0; BCP (0.2% solution) 0.4

I. Bacteriological Properties (a) Microscopic observation

Bacillus having a bacterial cell size of 0.6–0.7 μm×2–3 μm, one flagellum and mobility. Negative with respect to Gram's stain. No acidophilicity.

(b) Growth in/on various culture media (i) Bouillon agar plate culture (medium 1) Good growth. Colonies are circular with smooth surface and periphery, and they are yellow, translucent and lustrous.

(ii) Bouillon agar slant culture (medium 2) Fair growth. Colonies are filamentous, lustrous, yellow and translucent.

(iii) Bouillon liquid culture (medium 2) Fair growth with turbidity.

(iv) Bouillon gelatin stab culture (medium 3) Growth on the superficial layer with gelatin liquefaction.

(v) Litmus milk culture medium (medium 4) Decolored (after seven days) and peptonized.

(c) Physiological properties (1) Nitrate reduction and denitrification reaction (media 5 and 6)

Negative.

(2) MR test (medium 7)

Negative.

(3) VP test (medium 7)

Negative.

(4) Indole production (medium 8)

Negative.

(5) Hydrogen sulfide production (medium 9)

Positive.

(6) Starch hydrolysis (medium 10)

Positive.

(7) Utilization of citric acid (media 11 and 12)

Positive.

(8) Utilization of inorganic nitrogen sources (medium 13)

Negative with respect to nitrates; positive with respect to ammonium salts.

(9) Pigment production (medium 14)

Water-insoluble pigment produced.

(10) Urease (medium 15)

Negative.

(11) Oxidase (medium 16)

Negative.

(12) Catalase (medium 17)

Positive.

(13) Range of growth conditions (medium 2)

Growth temperature in the range of from 3° to 49° C., optimally from 23° to 37° C.

Growth pH in the range of from 5 to 10, optimally from 6 to 9.

(14) Behavior toward oxygen

Aerobic.

(15) O-F test (medium 18)

Oxidized.

(16) Production of acids and gases from saccharides (medium 19)

(+: produced; –: not produced)

| | Production of acid | Production of gas |
|---|---|---|
| 1. L-Arabinose | + | – |
| 2. D-Xylose | + | – |
| 3. D-Glucose | + | – |
| 4. D-Mannose | + | – |
| 5. D-Fructose | + | – |
| 6. D-Galactose | + | – |
| 7. Maltose | + | – |
| 8. Sucrose | + | – |
| 9. Lactose | + | – |
| 10. Trehalose | + | – |
| 11. D-Sorbitol | – | – |
| 12. D-Mannitol | – | – |
| 13. Inositol | – | – |
| 14. Glycerin | + | – |
| 15. Starch | + | – |

(17) Ice nucleus activity

The cell solution obtained by the cultivation in medium 2 is diluted with $10^7$ times its quantity of distilled water, a 2 ml portion of which is placed in a test tube having a diameter of 10 mm and cooled at –5° C. for 1 hour. "Positive" indicates "frozen" while "negative" indicates "unfrozen".

Positive. (Control distilled water with no additives is not frozen and thus is negative.)

(18) Phytopathogenicity toward tea

Negative.

The test performed in this connection is as follows:

On the leaves of a tea (*Thea sinensis* L. var. bohea) is inoculated a bacterium. The leaves which have been allowed to stand at a temperature of 27° C. and a humidity of 100% for one day are judged positive if the bacterium is proliferated at the part where it is inoculated while negative, if the bacterium is not proliferated.

(19) Tobacco hypersensitivity reaction

Negative.

In this context, a test is performed in accordance with the method described in Phytopathology, 77, 611–615 (1987).

II. Reason for the Judgment as a New Strain (i) Reason for the judgment of the present strain as belonging to *Xanthomonas campestris:*

As a result of the comparison of the abovedescribed bacteriological properties with those described in Bergey's Manual of Systematic Bacteriology (1984) and also with those of the known *Xanthomonas campestris* pv. campestris [Goto Masao et al., Nisshokubyo-Hou, 54, 192 (1988)], the present strain was judged as a strain belonging to *Xanthomonas campestris.*

(ii) Reason for the judgment of the present strain as a new strain:

The differences in bacteriological properties between the present strain and the three *Xanthomonas campestris* strains currently known will be shown below in Table 1.

TABLE 1

| Items of comparison | Present strain | Known strain A | Known strain B | Known strain C |
|---|---|---|---|---|
| Growth rate in YP agar plate culture | high (25° C. × 1 or 2 days) | normal (28° C. × 3 days) | | low |
| Growth temp. | | | | |
| Min. | 3° C. | | | 10° C. |
| Optimal | 23–37° C. | | | 33.5° C. |
| Max. | 49° C. | (generally 40° C. at maximum) | (generally 40° C. at maximum) | 42–43° C. |
| Oxidase | negative | negative | positive | |
| Utilization of malonic acid | negative | (generally utilized) | (generally utilized) | |

Note 1:

Strain A: obtained from the leaves of Florida citrus [Goto Masao et al., Nisshokubyo-Hou, 54, 196 (1988) and Minsavage G. V. and Stall R. E. (1986), Proc. 6th Int. Conf. Plant Path. Bact., 994–1004]

Strain B: *X. campestris* pv. translucens [Kim H. K., Orser C., Lindow S. E. and Sands D. C., Plant Disease, 71, 994–997 (1987)]

Strain C: obtained from tea buds (INAX) [Goto Masao et al., Nisshokubyo-Hou, 54, 189–197 (1988)]

Note 2:

Growth rate in the YP agar plate cuiture was judged as follows:

"high": when colonies were formed within 1 or 2 days

"normal": when they were formed within 3 or 4 days, and

"low": when they were formed in 5 days or more.

As a result of the examination of the difference between the present strain and the known strains, the present strain was distinguished from the known strains on the points shown in the above table, and thus judged as a new strain.

The present strain was deposited with Fermentation Research Institute, Agency of Industrial Science and Technology (the name of which was changed to National Institute of Bioscience and Human-Technology, Agency of Industrial Science and Technology on Jan. 1, 1993) at 1–3, Higashi 1 chome, Tsukuba-shi, Ibaraki-ken, 305 Japan, and accorded the accession number FERM P-12764 on Feb. 17, 1992. In this connection, the present strain was transferred on Feb. 17, 1993 to the aforementioned institute which is one of the international deposition authorities according to the Budapest Treaty, and accorded the accession number FERM BP-4191.

III. Cultivation of the Present Strain

As a method for the cultivation of the present strain, conventional methods for culturing *Xanthomonas campestris* bacteria can be generally emloyed. A specific example is aerobic cultivation using the aforementioned medium 14 or a liquid medium (medium 20) which is the same as medium 14 except for agar and conducted at a temperature of 25° C. for 1 or 2 days. In this context, industrially inexpensive sugars such as glucose, sucrose, maltose and Lactose, although not limited, are preferably employed as carbon sources. The culture media for the purpose of the present invention may be either liquid media or solid media, and preferably include, in addition to those described above, a solid medium such as the aforementioned medium 1, a liquid medium such as medium 2 which is the same as medium 1 except for agar, and the following medium 21:

Medium 21: meat extract 1.0; bacpeptone 1.0; $MgSO_4.7H_2O$ 0.05; $K_2HPO_4$ 0.05 (pH 7.0)

The present strain produces xanthan gum on the surface of the cells, so that they adhere easily to each other. On the other hand, as individual cells of the present strain, as will be apparent from the results in Examples 2 and 4, have ice nucleus-forming activity, culturing the individual cells which have been previously dispersed can be said more preferable than culturing adhering cells since the former culture will not require dispersion of the adhered cells and besides can freeze a large amount of water with a small amount of cells. Further, as will be apparent from the results in Example 3, it is preferred to culture the present strain in a medium (liquid medium) containing lactic acid.

In the cultivation of the present strain, the present inventors have also found, as a result of the following cultivation test, the fact that culturing the present strain in a medium containing lactic acid can intensively promote the growth of the cells.

Cultivation Test

Shake culture as pre-culture was carried out in the aforementioned medium 21 under aerobic conditions of 25° C. for 48.5 hours (about 2 days), and the culture solution thus obtained was inoculated into each of the liquid media specified in Table 2 below in a proportion of 1.5% before shake culture at 25° C. for 75 hours. Each of the culture solutions thus obtained was further cultured on an agar plate of medium 14 for 72 hours, and the number of cells in each culture was determined. The results are shown in Table 2.

TABLE 2

| Medium | Number of cells after 72 hours (cells/ml) |
|---|---|
| Basal medium (medium 21) | $1.5 \times 10^{10}$ |
| Basal medium containing no $K_2HPO_4$ | $1.5 \times 10^{10}$ |
| Basal medium containing no $MgSO_4.7H_2O$ | $1.3 \times 10^{10}$ |
| Basal medium containing 0.1% lactic acid | $2.0 \times 10^{10}$ |

It is apparent from the above results that the growth of the present strain is intensively promoted by adding lactic acid to the culture media. The content of lactic acid in a medium is preferably from 0.02 to 0.2%, more preferably from 0.05 to 0.15%.

The present invention also provides an ice nucleus-forming substance containing the new ice nucleus-forming bacterium described in the above paragraphs I, II and III. In this context, the phrase "containing the ice nucleus-forming bacterium" means that the main constituent for forming ice nuclei is *Xanthomonas campestris* INXC-1, and it is needless to say that the other components or raw materials may be appropriately contained, provided that they do not adversely affect the objects of the present invention. Typical examples of the ice nucleus-forming substance of the present invention include a culture product obtained by culturing the present strain, living cells collected from the culture product in a conventional manner, and a physical/chemical treatment product of the living cells as well as a dryed product thereof. The ice nucleus-forming substance also includes the so-called dead bacterium, i.e., ice nucleus-forming bacterium having no proliferating ability. By treating a bacterium under an ultra-high pressure of 300 MPa or more for 1–10 minutes, it is possible to kill the microorganism. Such sterilization, although depending on the numbers of cells to be treated, can be performed, for example, by treating $2.0\times10^{10}$ cells/ml under 300 MPa for 5 minutes to a survival rate of 1 cell/ml or less. In the ultra-high pressure treatment, the temperature should be set preferably lower than 28° C., e.g., in the range of from −20° C. to 28° C., more preferably from 0° C. to 10° C., from the standpoint of the ice nucleus-forming activity. Alternatively, by adding hydrogen peroxide and then leaving the resultant mixture to stand for a while, it is also possible to kill the present strain while keeping ice nucleus activity. For example, by adding an aqueous hydrogen peroxide in an amount of from about 0.05 to 0.1M as hydrogen peroxide to the culture solution and leaving it to stand at 10° C. for about 4 hours, it is generally possible to kill about $2.0\times10^{10}$ cells/ml to a survival rate of 1 cell/ml or less.

The ice nucleus-forming substance of the present invention can form nuclei of ice thereby freezing a substance, and thus it is preferably used in freezing a liquid food or in manufacturing artificial snow in a snow machine. Although the amount of the ice nucleus-forming substance used is not particularly limited, it is preferably used in a concentration such that will not impair the physical properties or taste of the liquid food in the former case, e.g., about one cell of ice nucleus-forming bacterium per ml of the liquid food, or in a concentration of one cell of ice nucleus-forming bacterium per drop of the aqueous suspension (ca. $1\times10^{-10}$–$1\times10^{-9}$ g/drop) in the latter case.

In an actual procedure for using the ice nucleus-forming substance in a snow machine, the ice nucleus-forming substance may be preliminarily added to the water to be supplied to the snow machine by which the water can be sprayed to be changed into snow, and the resultant mixture is then sprayed. The ice nucleus-forming substance is preferably added in a concentration such that individual droplets formed by spraying water contain at least one ice nucleus-forming bacterium. As a means for spraying, a spray nozzle for dual fluids which is suitable for making droplets (particle size: generally, 400–5 μm) by mixing air (compressed air) and water can be generally used. The liquid sprayed from the nozzle is diffused into an atmosphere generally cooled to 0° C. or less, preferably to −5° C. or less, and contacted with the cooled atmosphere whereby the water droplets are changed into snow. If the cooled atmosphere cannot be obtained under natural weather conditions, such an atmosphere may be prepared artificially. In preparing such a cooled atmosphere artificially, cooled air prepared, for example, by liquid nitrogen is generally preferably used for spraying where desired.

The ice nucleus-forming substance of the present invention can thus be used for freezing substances and does have the effect of promoting or facilitating the freezing of substances, and hence can be utilized, in addition to the cases mentioned above, for a variety of cases in which the freezing of substances is involved. Some examples of the utility forms of the ice nucleus-forming substance of the present invention include: the freezing of substances including foods such as vegetables, fruits, marine products, meats, milk, eggs, cereals, and processed foods (, e.g., ice cream, ice candies, sherbet, juices, sauces, soups and bean curd) by freezing these substances to which the present ice nucleus-forming substance has been already added by blending, spreading or pouring; the concentration of liquid foods such as vegetable juices, fruit juices, milk, fermented milk, egg liquid, alcoholic drinks, coffee, tea extracts, and liquid seasonings (, e.g., cooking vinegar, soy sauce and sauces), or the concentration of liquid substances such as industrial waste liquid by cooling these substances to which the present ice nucleus-forming substance has been already added, thereby partially forming ice and then removing the ice thus formed; the lyophilization of substances including foods such as fruit juices, coffee, tea extracts, liquid or semi-solid seasonings (, e.g., soy sauce, sauces, dressings, broths, fermented soy bean paste, and gelatinizable products such as agar) by lyophilizing by freezing these substances to which the present ice nucleus-forming substance has been already added and vaporizing moisture from the frozen substances thus obtained; the formation of an artificial ground by freezing the ground to which the present ice nucleus-forming substance has been already added; and the preparation of artificial rain containing the present ice nucleus-forming substance as an ice crystalline nucleus. Another example of the utility forms includes the softening of green vegetables which comprises spraying the present ice nucleus-forming substance over the surfaces of the green vegetables such as Nozawana, and cooling the whole vegetables artificially or under natural environment thereby to freeze the green vegetables partially or entirely.

The present invention is further described in detail hereinbelow with reference to Examples and Test Examples.

EXAMPLE 1 (Production of the Ice Nucleus-Forming Bacterium of the Present Invention)

New buds of tea obtained in a tea field in Morimachi, Shuchi-gun, Shizuoka-ken, Japan were suspended in a sterilized physiological saline solution and cultured on a Bacto Pseudomonas Agar F medium (medium 14) at 20° C. for three days to form colonies. These colonies were then suspended in water for isolating, as positive bacteria, ice nucleus-forming bacteria which could freeze upon cooling at −5° C. for 1 hour. The results indicated in the paragraph "I. Bacteriological properties" set forth hereinbefore were obtained by examining the bacteriological properties of the thus isolated strain, and the strain was designated as *Xanthomonas campestris* INXC-1.

EXAMPLE 2

(i) Preparation of the present ice nucleus-forming substance:

*Xanthomonas campestris* INXC-1 obtained in Example 1 was inoculated in the following culture medium 22 and shake-cultured under aerobic conditions at 25° C. for 1 day. By this culture, the concentration of the cells in the culture solution reached about $2.0\times10^{10}$ cells/ml. The cells obtained by separation from the culture solution were washed with sterilized distilled water and then diluted with the same distilled water to obtain a cell solution having the same concentration as the culture solution. The bacterium solution was subjected to pressurizing treatment at 5° C. under a pressure of 300 MPa for 5 minutes in a high pressure treatment apparatus (MFP-7000) manufactured by Mitsubishi Heavy Industries, Ltd. to sterilize the cells.

Medium 22:

| | | |
|---|---|---|
| Yeast extract (Difco) | 10 | g |
| Bactopeptone (Difco) | 10 | |
| $MgSO_4.7H_2O$ | 0.5 | |
| Lactic acid | 1 | |
| Water | 1000 | |
| (pH | 7.0) | (The pH was adjusted with 1 N NaOH.) |

The sterilized bacterium solution was lyophilized by a conventional method to obtain a powdery ice nucleus-forming substance. In this context, care was taken to maintain the temperature during lyophilization below 28° C.

(ii) Application examples of the present ice nucleus-forming substance:

Freezing of foods: (a) Freezing or concentration by freezing

To 5 liters of rice vinegar (acidity: 5%) was added 1 ml of the sterilized bacterium solution obtained as above diluted $10^3$ times, and the mixture was cooled at −6° C. for one day to form ice. When the ice was removed in a centrifuge for draining water from vegetables, rice vinegar which was concentrated to an acidity of 15% was successfully obtained in an amount of 1.5 liters.

As another application example, when 1 m of the same bacterium solution as above diluted $10^2$ times was added to 16 kg of egg white liquid, and the mixture was cooled to −18° C., the egg white liquid was successfully frozen without being supercooled.

On the other hand, rice vinegar to which no ice nucleus-forming substance had been added was supercooled at −6° C. and could not freeze within one day, and egg white liquid was also supercooled at −18° C. and required a considerable period of time for its freezing.

As still another application example, the same sterilized bacterium solution as was used in the case of rice vinegar was diluted $10^3$ times and added to 2.1 liters of white wine (Brix: 8.0, alcohol percentage: 13.0%) to a cell concentration of $2.0\times10^4$ cells/ml. The mixture was cooled at −10° C. overnight, and ice thus formed was removed by the same centrifuge as was used in the case of rice vinegar to obtain about 1.2 liters of a concentrated wine (Brix: 12.0, alcohol percentage 19.5%).

Alternatively, the lyophilized ice nucleus-forming substance obtained in the above paragraph (i) can also be used, by suspending it in water at 28° C. or lower in advance, for the concentration of cooking vinegar or wine, or for the freezing of egg white liquid in the same manner as is described above.

Freezing of foods: (b) Lyophilization

Two liters of deionized water at 25° C. was poured into a container containing 1 kg of tea to soften the leaves by swelling for 40 minutes. Twenty (20) liters of deionized water at 25° C. was then poured onto the tea leaves, and the mixture was stirred for 10 minutes to obtain an extract from the leaves. The extract thus obtained (cold water extract) was centrifuged.

Further, 20 liters of deionized water at 86° C. was poured onto the tea leaves, and the mixture was subjected to extraction for 10 minutes. The hot water extract was obtained by centrifugation and combined with the cold water extract previously obtained. The entire extract was then cooled to 5° C. A 1 ml portion, diluted $10^3$ times, of the same sterilized bacterium solution as was used in the above paragraph "Freezing of foods (a)" was added, and the mixture was cooled at −6° C. for 1 day to form ice.

The ice was removed by centrifugation to obtain a 10-fold concentration of the tea extract, which was then directly lyophitized to prepare an instant tea.

Production of artificial snow (a):

The sterilized bacterium solution obtained as described in the above paragraph (i) was diluted with water, and 50 drops of 5 μl were placed on a glass plate and cooled at −5° C. for 5 minutes.

The number of sterilized bacterial cells per 5 μl and that of frozen drops are shown in Table 3.

TABLE 3

| Bacterial cells | Frozen drops |
|---|---|
| 100 | 50 |
| 10 | 50 |
| 1 | 50 |
| 0.1 | 9 |
| no addition | 0 |

These results indicate that none of the drops to which bacterial cells had not been added was frozen, while the drops containing the ice nucleus-forming substance of the present invention were successfully frozen.

Therefore, it can be seen that the drops containing the ice nucleus-forming substance of the present invention can be used in the production of artificial snow by freezing them at a temperature below the freezing point but higher than would be required for the drops containing no ice nucleus-forming substance.

Alternatively, the lyophilized ice nucleus-forming substance obtained in the above paragraph (i) can also be used, by suspending it in water at 28° C. or lower in advance, for the production of artificial snow in the same manner as is described above.

Production of artificial snow (b):

A water dilution of the sterilized bacterium solution obtained as described in the above paragraph (i) was sprayed in the field at a temperature of −7° C. using a snow machine equipped with a nozzle for dual fluids and compressed air to make snow artificially.

In this context, the dilution had a cell concentration of about $2.0 \times 10^6$ cells/ml. Droplets (waterdrops) produced by the spraying had an average particle diameter of about 100 μm.

EXAMPLE 3 (Method for Culturing the Present Ice Nucleus-Forming Bacterium)

The present strain was inoculated separately in the following medium 23 to which one of glucose, maltose and sucrose had been added in a concetration of 0.1% and in the medium 22 to which 0.1% of lactic acid had been added, and each inoculated medium was shake-cultured at 25° C. for one day.

Medium 23:

| | | |
|---|---|---|
| Yeast extract (Difco) | 10 | g |
| Bactopeptone (Difco) | 10 | |
| $MgSO_4.7H_2O$ | 0.5 | |
| Lactic acid | 1 | |
| Water | 1000 | |
| (pH | 7.0) | (The pH was adjusted with 1 N NaOH.) |

Each of the culture solutions was serially diluted 10-fold in test tubes, and the respective dilutions were individually charged in an amount of 2 ml into ten test tubes having a diameter of 10 mm and cooled at −5° C. for 1 hour. For the respective culture solutions, the dilution magnification at freezing and the number of frozen tubes at the dilution magnification are shown in Table 4.

TABLE 4

| Dilution | Glucose | Maltose | Sucrose | Lactic acid |
|---|---|---|---|---|
| $10^7$ | 10 | 10 | 10 | 10 |
| $10^8$ | 5 | 4 | 5 | 10 |
| $10^9$ | 0 | 0 | 1 | 10 |
| $10^{10}$ | 0 | 0 | 0 | 10 |

It is apparent from the results shown in Table 4 that the higher the dilution magnification, the lower the ice nucleus-forming activity in the case of the addition of sugar in comparison with the case of the addition of lactic acid. Just after the cultivation, it was observed in the case of the addition of glucose, maltose or sucrose that the cells began to agglomerate and soon precipitated when left standing. However, in the case of the addition of lactic acid, no agglomeration occurred and thus no precipitation was observed. Therefore, it has been found that, when cultivation is conducted in the presence of lactic acid, the present strain does not agglomerate but exhibits ice nucleus-forming activity even at a higher dilution magnification.

EXAMPLE 4

*Xanthomonas campestris* INXC-1 obtained in Example 1 was inoculated in medium 22 and cultured under aerobic conditions at 25° C. for 1 day. After the cultivation (cell concentration: $2.0 \times 10^{10}$ cells/ml), the cells were washed with sterilized distilled water and diluted with the same distilled water to obtain a cell solution having the same concentration as the culture solution. The bacterium solution was pressurized under the conditions of 100–400 MPa at 5° C. for 5 minutes in a high pressure treatment apparatus (MFP-7000; manufactured by Mitsubishi Heavy Industries, Ltd.). The number of viable cells after each treatment was determined by an agar plate culture method. The results are shown in Table 5.

TABLE 5

| Pressurizing conditions | Viable cells (per ml) |
|---|---|
| non-treated | $2.0 \times 10^{10}$ |
| 100 MPa | $1.5 \times 10^{10}$ |
| 200 MPa | $1.2 \times 10^3$ |
| 300 MPa | <1 |
| 400 MPa | <1 |

It is apparent from the results of Table 5 that pressurizing treatment under 300 MPa for 5 minutes kills the present strain to 1 cell/ml or less. In this context, even in this case, in respect of ice nucleus-forming activity, there is no difference between the sterilized strain and the present living strain.

INDUSTRIAL APPLICABILITY

The new strain *Xanthomonas campestris* INXC-1 of the present invention is not only negative with respect to phytopathogenicity toward tea, but also negative with respect to tobacco hypersensitivity reaction in which bacteria which are negative with respect to tobacco hypersensitivity reaction are generally free of phytopathogenicity. Besides, this new strain is an ice nucleus-forming bacterium having a high growth rate during culture, so that it has become possible for the first time to provide a novel ice nucleus-forming bacterium and ice nucleus-forming substance by which the objects of the present invention have been accomplished. Therefore, the ice nucleus-forming substance of the present invention can be expected to be applicable much more extensively to a variety of fields in which the freezing of substances is involved as compared with conventional ice nucleus-forming bacteria.

What is claimed is:

1. A method for freezing a substance which comprises (a) adding to the substance to be frozen an ice-nucleus forming substance containing *Xanthomonas campestris* FERM BP-4191; and (b) cooling said substance to be frozen to a temperature at which the substance to be frozen freezes.

2. The method according to claim 1, in which the substance is a food.

3. The method according to claim 2, in which the food is selected from the group consisting of vegetables, fruits, marine animals, meats, milk, eggs, cereals, and processed foods.

4. The method of claim 3, wherein the processed food is ice cream, ice candies, sherbet, juices, sauces, soups, bean curd or agar.

5. The method according to claim 1, in which the addition is conducted uniformly on the whole substance to be frozen by blending, or non-uniformly by pouring on a surface of the substance to be frozen or by contacting the ice nucleus-forming substance with the surface of the substance to be frozen.

6. The method according to claim 5, in which the substance is a green vegetable, and the addition is conducted by pouring on a surface of the vegetable.

7. The method of claim 6, wherein the green vegetable is Nozawana.

8. The method according to claim 1, in which the substance to be frozen is the ground, and which further comprises freezing the ground to make an artificial frozen ground.

* * * * *